(12) United States Patent (10) Patent No.: US 7,677,798 B2
Ohnona et al. (45) Date of Patent: Mar. 16, 2010

(54) SYSTEM INCLUDING A PORTABLE DEVICE FOR RECEIVING DENTAL IMAGES

(75) Inventors: Meyer Ohnona, Paris (FR); Jacques Sebag, La Celle-St Cloud (FR)

(73) Assignee: Visiodent, La Plaine Saint Denis (FR)

( * ) Notice: Subject to any disclaimer, the term of this patent is extended or adjusted under 35 U.S.C. 154(b) by 230 days.

(21) Appl. No.: 11/868,054

(22) Filed: Oct. 5, 2007

(65) Prior Publication Data

US 2008/0084965 A1 Apr. 10, 2008

(30) Foreign Application Priority Data

Oct. 6, 2006 (FR) .................................. 06 08777
Feb. 21, 2007 (FR) .................................. 07 01242
Sep. 20, 2007 (FR) .................................. 07 06613

(51) Int. Cl.
*A61B 6/14* (2006.01)
(52) U.S. Cl. ........................................ 378/191; 378/98
(58) Field of Classification Search ............. 378/38–40, 378/98, 98.8, 168, 191, 204
See application file for complete search history.

(56) References Cited

U.S. PATENT DOCUMENTS

2004/0184643 A1    9/2004    Stantchev .................... 382/128
2005/0053199 A1    3/2005    Miles ......................... 378/197

FOREIGN PATENT DOCUMENTS

DE         25 05 798        8/1976
DE         200 02 671       5/2000
FR         2 876 572        4/2006

*Primary Examiner*—Courtney Thomas
(74) *Attorney, Agent, or Firm*—24IP Law Group; Timothy R. DeWitt

(57) ABSTRACT

The system for taking images includes a portable base (2) for managing an image sensor (1) used to take the image of a tooth, providing an electronic image which is transmitted to display circuits (80), and it includes sequencing circuits, which respond to the action of image file validation circuits, the sequencing circuits managing a library, for filing a sequence of image files, by associating, with each validated image file, rank sequence data in the sequence.

21 Claims, 7 Drawing Sheets

SYSTEM INCLUDING A PORTABLE DEVICE FOR RECEIVING DENTAL IMAGES

CROSS-REFERENCE TO RELATED APPLICATIONS

The present application claims priority to and the benefit of the filing dates of French Patent Application Serial No. 06 08777 filed on Oct. 6, 2006, French Patent Application Serial No. 07 01242, and French Patent Application Serial No. 07 06613 filed on Sep. 20, 2007.

STATEMENT REGARDING FEDERALLY SPONSORED RESEARCH OR DEVELOPMENT

None.

BACKGROUND OF THE INVENTION

1. Field of the Invention

The present invention relates to a system including a portable device that consists of a base for receiving dental images taken with an X-ray sensor.

2. Brief Description of the Related Art

Equipment used for taking dental images usually includes a PC connected to a small electronic device, generally of the size of a cellular phone, which is used as an interface which is dedicated to supplying the desired clock signals to the sensor, and which is of the electrical charge transfer (CCD) type, to recover these charges and digitize the quantity as image data-defining image elements (pixels). The base may thus be placed near the patient and connected to the CCD sensor by means of a relatively short cord, which limits the electronic noise that disturbs the electronic signal of the charges.

However, the ergonomics of the equipment still leaves something to be desired. In fact, the practitioner must, on the one hand, locate the sensor at a precise point in the mouth of the patient and, on the other hand, control the equipment, i.e. he must activate the X-ray source and manage the images that are taken; in other words, he must examine them, and delete, in real time, those of insufficient quality, so that he may take another one. He must also file them.

In particular, in order to check the quality of the image that has just been taken, the practitioner must temporarily leave the base and move to the PC in order to activate a display program therein. He must also select the last image received by the PC, so that he may check its quality.

Filing involves opening the patient's electronic file in the PC and transferring to it each new image taken, by associating service information to it which specifies the position of the tooth in the jaw and the date the image is taken.

These tasks—examination and filing of the images thus obtained—consequently represent a large amount of work for the practitioner.

The object of the present invention is to provide a solution that is less burdensome to the practitioner, for addressing at least one of the above problems, by facilitating the filing process and the examination of the quality of the images taken.

SUMMARY OF THE INVENTION

For this purpose, the invention relates first of all to a system for taking dental images, including a portable base for controlling an image sensor capable of taking an image of a patient's tooth, and which is responsive to the intensity of radiation emitted by an external X-ray source and which is adapted to provide an electronic image that corresponds to the tooth through which the radiation travels, and in which the base is adapted to receive the electronic image and which includes a means for displaying the image, with said system including sequencer means that are responsive to the action of validation means used for validating at least one file which is an image file of said dental images, in which the sequencer means are adapted to manage a library, for storing a sequence of files of said dental images, and adapted to associate rank sequence data with any validated image file.

The above system may, as a whole, comprise a base as specified, which is completed by the desired functional circuits which provide the other functions of the system, as described above. However, some of these circuits may also be provided outside of the base. In this way, the library may be part of the base or may be external to it, for example in a local PC used for processing images, or also in a server that is accessible through a data transmission network, such as, for example, the Internet or a local area network (LAN).

As explained hereinafter, associating the rank sequence data with the image files may be carried out according to many embodiments.

The embodiments may be of two types, the first type, purely "software", which essentially uses hardware means which are common to other functions, i.e. a central unit of a computer, or of the base, associated with an application software, and the second type, which is purely "hardware" or mixed "hardware-software" using, exclusively or in addition to the first type, circuits which are specialized for the desired function, with, if necessary, software that is limited to the general management of the function being considered, if the circuits can handle all the detail in this management. Two embodiments of the second type are described below.

In the first embodiment, it is possible to write in any desired memory area of the library, and the rank sequence data are explicitly written in association with the image file being considered. In the second embodiment, the rank sequence data will not be stored as such, however they will be used to define, in a objective manner, a specific memory area address for the image file having a rank sequence j being considered.

The sequencer means include, for example, a counter, which is adapted to be incremented by the validation means, in order to provide, at the output, validated image counting data that are part of said rank sequence data.

In this way, even though the sensor must take an increasing number of images, to compensate for the presence of defective images, the counter will remain in phase with the rank sequence of the tooth's image since the counter does not sense image files that are not validated.

As pointed out above, in the first embodiment, the sequencer means may be adapted to write the counting data associated with the image file being considered into the library, or else, according to the second embodiment, the sequencer means are adapted so that the counting data control a switching circuit that determines, from among a plurality of specific addresses, an address where the file in question is to be written into the library.

Sequencer means may also be provided that are adapted to writing the image files of all the images taken into the library, whether validated or not, as well as the rank sequence data associated with the data of said validation.

In such a case, the sequencer means are preferably adapted to supplying the data of said validation in the form of time-stamped data from the associated image file.

Processing is therefore particularly simple, since known operating systems provide time-stamped data. When processing the images, it is therefore the most recent image file which must be selected, from among a possible plurality of image files having a same rank sequence j.

Advantageously, the library contains a plurality of memory areas for the same plurality of patient files, including some said dental image files and a history of the care of the patient being considered, and a sleep/wake device is adapted to additionally control managing library circuits, and which are provided for, on the basis of information on the treatment sequences forecast for the day's patients, automatically selecting one of the memory areas of patient files and providing information from the file on the display means.

This involves, therefore, an "auto-dial on pickup" function, through which the practitioner automatically addresses the desired file, with a reference to the file being kept, for example, in a list in an agenda that indicates the patients to be treated during the day being considered, so that the files, in whole or in part, are displayed consecutively on the display means, according to their rank sequence in the list, and where the transition from one file to the next is controlled by the sleep/wake device.

The invention additionally concerns software used for managing the taking of dental images, and which comprises a series of instructions arranged for, once they are made accessible to a computer processing system, managing the input of a sequence of dental images.

The software may for example be incorporated, in whole or in part, into the base or into a local computer associated with the base, or even into a server which may be accessible to a local or worldwide data transmission network, such as the Internet. It will be noted that this software may also be used in a base for taking images which would not be provided with some of the functions indicated above, such as for example a display and means that are associated locally for the processing of the images and their inhibition. In fact, managing the taking of such a sequence of images is of great practical interest to the practitioner, even if he could not examine the current image on the base.

The series of instructions is advantageously arranged so that the input images are automatically filed in a predetermined order.

The invention also concerns a medium for data storage, which contains software for managing the taking of images according to the invention. This data medium may be incorporated into the base or, more generally, into the above system, or it could even be located in a remote server that is accessible through a data transmission network.

Advantageously, the base includes control means for invalidating the image, with, preferably, means for processing the image.

In this way, the base constitutes a tool by means of which the practitioner can very quickly invalidate any image which does not suit him and immediately order another image to be taken.

Although the invention as disclosed herein is perfectly suitable for facilitating the work of a dentist, it will be noted that it remains no less true that the invention can be used for taking images other than dental images, and/or for obtaining them from a source of illumination that is different from a source of X-rays. Indeed, the invention per se is independent of the nature of the source of illumination and is also independent of the nature of the images received. For example, the above base may be used to inspect a metal or reinforced concrete structure, by passing X-rays through the material being considered, or simply by illumination and capture of an image as obtained by the reflected radiation, which may therefore be a radiation that is not as hard as X-rays, for example, in the visible or infrared range.

It will be noted that the function of inhibiting defective images, which can be provided by the base, may be performed by the above means of validation, since the selection among the images of acceptable quality and the defective images may be made by highlighting the images of acceptable quality with an electronic stamp, where the highlighting therefore indicates this quality, or else this selection may be made by highlighting the defective images, where this latter highlighting therefore indicates that inhibition of the image is recommended, or at least that its use be inhibited.

It may also be noted that, in an application in which the risk of obtaining an image of insufficient quality is believed to be low, a degraded mode of operation may then be provided, in which neither the inhibition nor the validation of the images would take place, i.e., the corresponding hardware and/or software means may then be omitted. Means for controlling the taking of images, such as for example a button or a circuit that programs the time lapse between two automatic image-taking sessions in a preprogrammed sequence, will therefore be substituted for the validation means for advancing the sequencer means. In other words, the command for a new image-taking session constitutes an implicit invalidation of the previous image. Even if the user is no longer in a position to invalidate an image, he nevertheless benefits from the function that automatically numbers the images taken in sequence, which already offers a significant advantage.

The base advantageously includes mounting means for mounting the same onto a piece of furniture, so that the base be carried by, and perhaps even be incorporated into, the piece of furniture, for example a support arm for a source of X-rays or even a tray or a support bracket for dental tools such as drills, since such an arm or bracket is located near to the patient. The base may be supported by an arm or the arm-rest of an armchair or equivalent piece of furniture, for example, provided for the practitioner or the patient. Since the assembly is essentially based on mechanical characteristics, it will be noted that such an assembly on a piece of furniture would be considered for any base having electronic characteristics that differ from those of the invention.

The base may, for example, include a casing that is provided with two flexible straps, and which includes means for mutual hooking that will close a buckle around the arm. It is also possible to consider a clip made of two opposite rear and lateral tongues which are spread apart substantially along the width of the arm so that it is elastically tightened, possibly with a hook, at one free end of one of the tongues, so that it constitutes a pawl that abuts a rear wall of the arm.

The base may include a casing that consists of a piece of furniture and which includes a housing for receiving the remainder of the base, i.e., its circuits, in which the housing including a window for showing a screen of the means of image display, and for showing a control device associated with said means of ordering invalidation.

The housing of the casing may, in particular, extend along a direction in which the support arm extends, partly in front of the window and partly in a portion of the arm portion that has no window, and means for processing the image are assembled in a module which is separate from the screen but which is connected to this screen with flexible wires, or through a short-range link, for example radio or infrared.

In a preferred embodiment, the present invention is a system for taking dental images in which the system comprises an image sensor for taking a dental image of a tooth of a patient, said image sensor being responsive to an intensity of radiation emitted by an external source of X-rays and being adapted to provide an electronic image corresponding to the tooth through which the radiation travels, and a portable base for controlling said image sensor and for receiving said dental image from said image sensor. The portable base comprises means for displaying a dental image and sequencing means responsive to an action of a validation means used for validating at least one image file of dental images, at least one file being an image file of a said dental image, wherein the sequencing means are adapted to manage a library, for storing a sequence of files of said dental image files, and which are adapted to associate rank sequence data with each validated image file. The sequencing means may comprise a counter adapted so that it is incremented by the validation means to provide counting data at an output for validated image files belonging to said rank sequence data. In one embodiment, the sequencing means is adapted to write, in the library, the counting data in association with the image file being considered. In another embodiment, the sequencing means is adapted so that the counting data control a switching circuit which determines, from among a plurality of specified addresses, an address where to write, in the library, the image file being considered. In still another embodiment, the sequencing means are adapted to write, in the library, the image files of all the images that were taken, whether validated or not, as well as the rank sequence data that is associated with validation data. In yet another embodiment, the sequencing means are adapted to write, in the library, the image files of all the images that were taken, whether validated or not, as well as all the rank sequence data that is associated with validation data, and the sequencing means are adapted to provide the said validation data in the form of time-dated data of the associated image file.

The library contains a plurality of memory areas for a same plurality of patient files including some said files of dental images and which includes a care history of the patient considered, and wherein the base comprises a sleep/wake device that is arranged to control managing circuits of the library, provided for, according to information on a planned sequence of patients to be treated for one day, automatically selecting one of the memory areas of patient files and providing file information on the display means.

The base may further comprise invalidation means for controlling invalidation of an image file. The display means may be adapted so that they automatically display a last image received by the base, and accessing means are provided for processing the image. In another embodiment, the display means are adapted for automatically displaying a last image received by the base and processing means are provided for processing the image, including code conversion circuits adapted for converting gray levels, encoded on a scale of predetermined gray levels, into elements each having a specified color which belongs to a predetermined corresponding scale of colors.

In still another embodiment, the display means are adapted for automatically displaying a last image received by the base, and means are provided for processing the image, which include code conversion circuits arranged for converting gray levels, encoded on a predetermined scale of gray levels, into elements each having a specified color belonging to a predetermined corresponding scale of colors, and the base includes a man-machine interface unit that is adapted for controlling the displacement of a cursor in a predetermined range in order to cause a variation of connection between each level of the scale of gray and the associated specified color, wherein the cursor includes a wobulation circuit comprising a clock signal counter associated with control circuits which cyclically count between two limit values, in order to thus provide an upgradeable value of a conversion pitch between the scale of gray levels and the scale of colors.

The base may further comprise digital link means adapted for receiving, from an item outside the base, animated images that are provided at a given rate, and the display means are adapted for displaying said images. The base may have digital link means adapted for receiving programming data from outside the base.

In another embodiment, the base comprises a housing, for receiving the image sensor at rest, associated with a detector of the presence of the image sensor adapted for controlling a standby/reviving device arranged for controlling managing circuits for managing the image sensor. The base may further comprises means for mounting the base on a piece of furniture.

In another embodiment, the base further comprises a casing comprising of a furniture element and including a housing for receiving other parts of the base, with a window for displaying a screen of image display means and means for presenting a control element belonging to the image invalidating control means.

In another embodiment, the base further comprises a casing comprising of a furniture element and which includes a housing for receiving other parts of the base, with a display window for the screen in the image display means and which has a control element belonging to the image invalidating control means, the housing of the casing extending, along a direction in which a support arm extends, and which constitutes the piece of furniture, partially in front of the window and partially in a section of the arm that has no window, and means for processing the image are grouped into a module which is separate from said screen and is connected to the screen with flexible wires.

In another embodiment, the base further comprises a casing comprising a piece of furniture and which includes a housing for receiving other parts of the base, with a window that reveals a screen in image display means and which displays a control element belonging to image invalidating control means, with the base being adapted to be incorporated into either a support arm of a source of X-rays or a support bracket for dental tool.

In another embodiment, the present invention is software for managing the taking of dental images, characterized by the fact that it includes a series of instructions arranged so that, once they are made accessible to a computer operating system manage the reception of a sequence of dental image files. The series of instructions may be adapted so that the received images files are automatically filed in a predetermined order.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

The invention will be better understood with reference to the following description of a preferred embodiment and of alternatives of a system, with a base, according to the present invention, with reference to FIGS. 1-8.

The invention involves three aspects, in which the first aspect provides, first of all, the architecture of the system according to the invention, i.e., the architecture of the base and that of an associated managing computer, as well as that of a bidirectional link connecting them, and also provides functions, linked to the images taken, and provided by the base, in which the second aspect exhibits physical aspects, concerning a base casing, and in which the third aspect exposes various embodiments for the automatic management of the images, in particular their automatic numbering.

Figure 1:
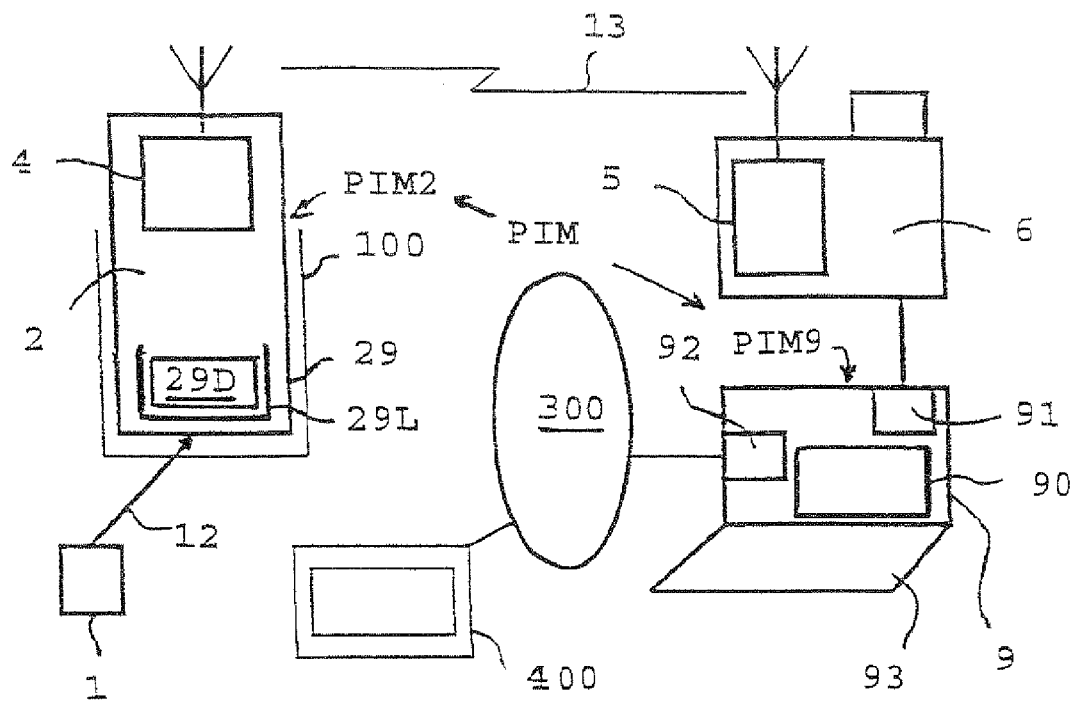
FIG. 1 is a schematic representation of a piece of equipment for taking dental images, consisting of a base according to the invention.

According to the first aspect, FIG. 1 is a schematic representation of an image sensor 1, which here is connected by a data transmission cord 12, to a base 2 for managing sensor 1. Base 2, in this example, is connected by a digital data transmission bidirectional link, which here includes here a section with radio link 13, to a computer for processing input dental images, which here is a personal computer, PC, referred to as 9, in which a screen 90 and a keyboard 93 are used as a man-machine interface. The digital link here is established through radio circuits 4 connected to base 2, and which here are incorporated into a portable casing 29 of base 2, said casing 29 being removably installed in a support base 100. The radio circuits 4 are also connected, through radio link 13, which here is about 15 Mb/s, to homologous radio circuits 5 which are part of an adapter module 6 which constitutes a peripheral of PC 9 to which it is connected by means of a wire through a port 91 of PC 9. The radio link 13 here is of the WiFi type. The adapter module 6 adapts the physical level of the data as well as their format and their transmission speed, all this from the radio link 13 towards port 91 and vice-versa. The adapter module 6 thus processes, in particular, the OSI layers of physical level 1, and of adaptation level 2. Here PC 9 is connected, via interface circuits 92 which allow a downloading, to a server 400, through a data transmission network, here the Internet 300.

Figure 2:
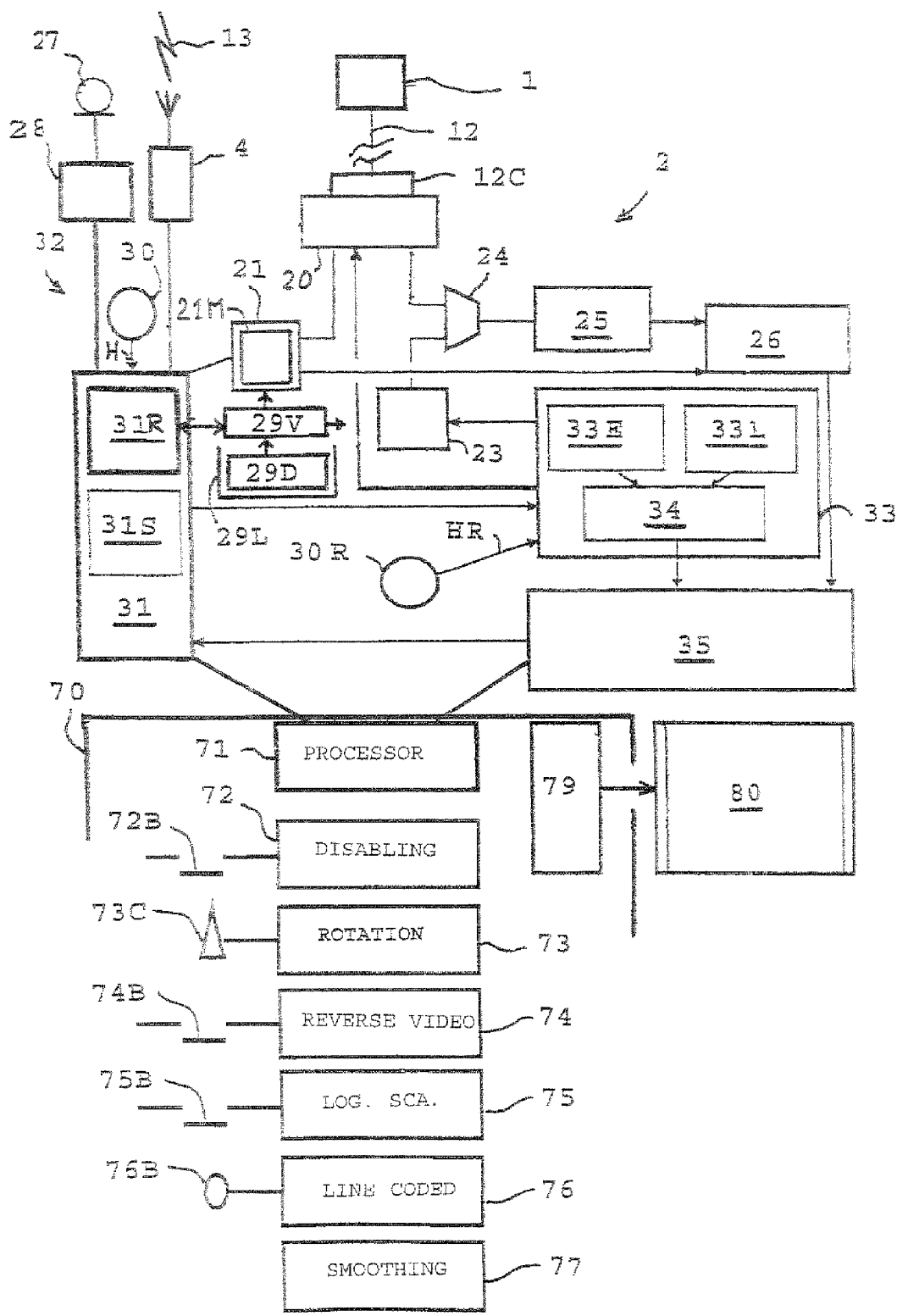
FIG. 2 is a functional diagram of the base.

FIG. 2 illustrates sensor 1 and the circuits of base 2. The upper part of FIG. 2 corresponds to analog interface circuits connected to sensor 1 as well as to radio circuits 4 through the other circuits, i.e., digital circuits, of base 2.

The digital circuits include a central managing unit for base 2, with said central unit here being essentially limited to a microprocessor 31, and which, in this example, include signal processing circuits 31S and conventional circuits, not shown, for storing software for controlling microprocessor 31, and also including, as needed, attached memories containing, for example, control data for the other circuits. A time base 30 provides a clock signal H which controls microprocessor 31.

A circuit 33, called a user-programmable network, and usually called FPGA, for Field Programmable Gate Array, is controlled by microprocessor 31, i.e., it operates as a slave of microprocessor 31 at the pace of a fast clock signal HR originating from a rapid oscillator 30R, which in fact may be a stage upstream in the time base 30, i.e., clock signal HR has a higher frequency than that of clock signal H.

Programmable circuit 33 controls a random access memory 35, RAM, which is connected at the output to radio circuits 4 through microprocessor 31, and said random access memory is used as a buffer between sensor 1 and radio circuits 4, which transmit image data to PC 9. For this purpose, programmable circuit 33 includes two registers, 33E and 33L, for addressing memory 35, for writing and reading respectively. A switching multiplexer circuit 34 with two input channels, each provided for transmission in parallel of about twenty bits, receives the outputs of the two registers 33E and 33L on two parallel inputs of the respective channels for switching one of the two outputs towards address inputs of memory RAM 35. A bit for controlling writing or reading is, for this purpose, applied on a switching control input of switching circuit 34 and on an operating mode control input, for writing or reading, of memory 35. Each writing or reading cycle is directly controlled by memories which are internal to programmable circuit 33, thus storing the desired sequencing program, with said sequencing, in particular, carrying out the incrementation, through two respective clock signals, of two counters of writing and reading respectively, not illustrated. Outputs, which are respectively parallel to the two counters, may alternately be switched, through a switching circuit (multiplexer with two parallel input channels connected to the two respective parallel outputs), towards address inputs of the above internal memories.

Nevertheless, through a link provided to this effect, microprocessor 31 may, through programmable circuit 33, for example, control the reading of memory 35, i.e., its rate, according to the instantaneous transmission possibilities provided by radio circuits 4 and 5. Thus, in case of a fault in the radio transmission of a block or packet of bits, radio circuits 5, which now operate as receivers, may in return control a re-transmission of the bits. These bits may then be directly re-transmitted from microprocessor 31, if it has temporarily kept traces thereof, or be re-read in memory 35 at any desired moment, between two elementary writing cycles of a bit or a block of a few bits. The operation is thus intertwined between writing and reading.

The series of circuits 30, 30R, 31, 33 and 35 thus constitutes a sequencer 32.

The analog circuits of base 2 include an interface managing circuit 21 which is controlled by microprocessor 31 and FPGA circuit 33 for controlling the sequencing of the taking of images by sensor 1 and its reading by means of circuits 23, 24, 25, which are controlled in synchronism with sensor 1, in order to format and sample the image signals originating from sensor 1, here based on CCD circuits, i.e., analog signal shift registers, with transfer by charge coupling. Other types of sensors could be used, for example those based on C-MOS.

Circuit 23 is a sampling circuit which receives, from programmable circuit 33, a clock signal at about 1 MHz and which, at this rate, provides a short pulse that briefly opens an analog gate 24 which connects, through a connector 20 which receives an end connector 12C on cord 12, an output of CCD sensor 1 to an input of an analog shift register 25 which supplies an analog-digital converter, CAN, 26. In response, CAN 26 provides a value of fourteen bits which represents the amplitude of the analog signal received, i.e., the quantity of X-rays received for a predetermined period by the elementary pixel detector that has the corresponding reading rank sequence. This period is defined between an initialization instant of CCD sensor 1, by purging parasite charges, and a control instant of the end of integration of the electric charges induced by the X-ray radiation in each elementary "casing" defining a detector and integrator capacitor which is insulated from other similar capacitors, and which represents such an elementary pixel detector. The instant the integration end is followed by an instant of transferring the charges, which were accumulated in each detector and integrator capacitor, towards an associated memory cell in CCD sensor 1. The cells are connected in series to be consecutively read by consecutive shifts and output towards base 2.

Thus, each microsecond, 14 bits are transmitted from CAN 26 to memory 35 and are memorized therein as explained. Programmable circuit 33 controls, by clock signal transmission, the reading rate of sensor 1, and also controls the rate of downstream circuits which extend up to the CAN 26, as well as the writing rate in memory 35.

Base 2 includes an electronic-circuit processing unit 70 for processing images and for controlling the display of a display screen which is part of a display 80 incorporated into one side of casing 29, in order to display the images of sensor 1 which are successively stored in memory 35. Processing unit 70 is managed by a microprocessor managing block 71 which is connected bidirectionally to microprocessor 31.

To clarify this presentation, processing unit 70 has been illustrated as a separate block. However, it may be possible for hardware and software elements of processing unit 70 to be part of microprocessor 31, either as specific elements dedicated to the desired function, or, preferably, as elements which are common to the various functions of microprocessor 31 and whose functions are used in time sharing.

Processing unit 70 includes a number of functional blocks for the management and the processing of the images provided by sensor 1.

Thus, a display control block 79 permits the formatting of the image signals into the desired format for the screen of display 80. For ease of processing, the processing unit 70 systematically receives a copy of the last image received by memory 35 and it thus displays it automatically. There is therefore no need to input image selection controls. It will, however, be noted that it may be provided that the practitioner will have controls available to him that will enable him thereafter to substitute a previous image for the present image.

A block 72 for processing the invalidation of the last image taken allows this image in memory 35 to be deleted, under the control of a delete button 72B, if the image restored on the screen of display 80 is not satisfactory. Thus, any future processing of the image is inhibited. Display 80 thus constitutes a viewfinder which is remote with respect to image-taking sensor 1. As an alternative of the above physical deleting, button 72B controls a logic deleting, i.e., an inhibition of any processing of the image, by the addition, to the image in memory 35, of service data indicating, to any downstream operating circuit, that the image is invalid. Button 72B may be a real button or the image of such a button presented in an area of the screen of display 80, with this area being selected by a pointer of the mouse type, or by finger pressure or using the end of a stylus if a touch screen is provided. The same is true with respect to the other buttons or cursors of man-machine interface indicated hereinafter for the other image managing functions.

A functional rotation block 73, allows, using a cursor 73C, a progressive rotation of the image to be performed in either direction. Cursor 73C may be a rotary or linear potentiometer or the image of such a cursor as shown on the screen of the display 80. The rotation block 73 then transcodes, using a transcoding table, a command from cursor 73C into the value of an angle of rotation. Since the rotation center is presumed to be at the center of the image, the radius of rotation of each point, or pixel, of a source image, obtained from memory 35, is then calculated in order to determine its new pixel position in a target, final, desired image. The practitioner may thus take an image under a mechanically optimal angle with respect to the introduction of the sensor in the mouth of the patient, and he may then straighten up this image for his preliminary examination and later processing.

A functional block 74 includes inverter transcoding circuits which allow a person to perform a reverse video of the image by control with a button 74B. In such a case, the various digital values, which represent the respective levels of gray of various pixels in a source range extending from a zero value to a maximum value, are subtracted from the maximum value in order to thus invert the scale of values in this range. The above subtraction operation may be replaced, with substantially the same result, by an inversion of each bit of each value of gray level being considered, according to the well known principle of the 2's complement of a binary number representing the level of gray. The zero value of the source range may therefore, as needed, represent either the black level or the white level. The radiological image, which is of course in negative, can therefore be presented either in negative or in positive. Since the perception of gray levels by the human eye is not linear, it is of interest to note that certain gray levels will be better perceived if they are transposed to the other half, dark or light, of the gray range.

Figure 3:
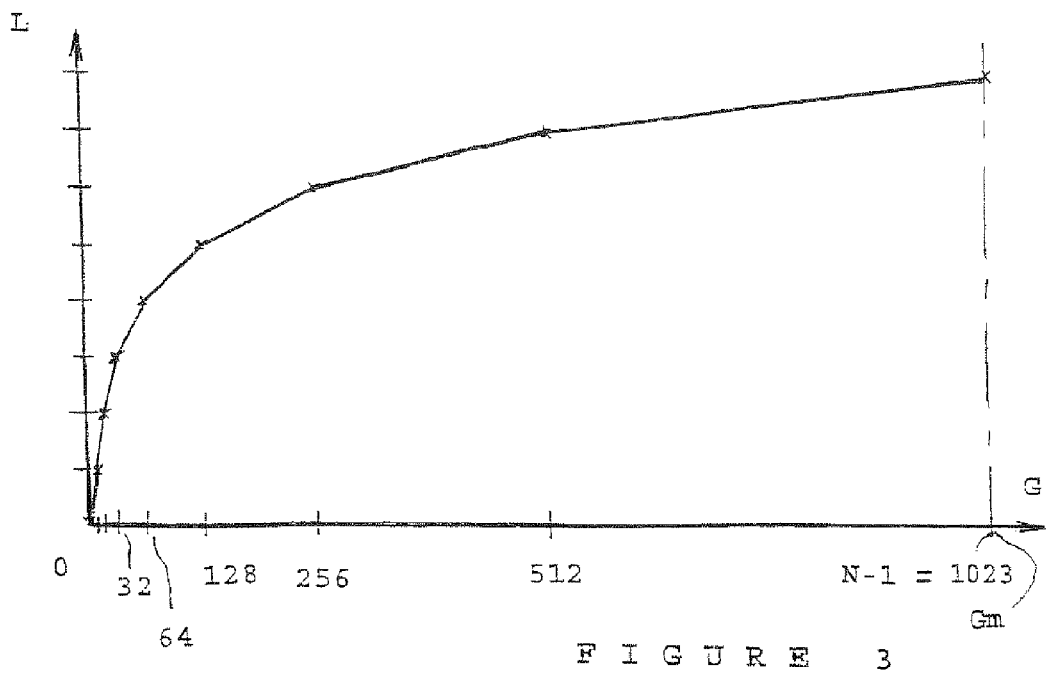
FIG. 3 illustrates a sensitivity conversion curve for the levels of gray in an image.

A logarithmic converter 75 allows the execution of a code conversion in order to expand or compress an area of the range of gray source levels of one end side or of the other end side, that is to say to translate any gray level, located on either side of the range, according to a given value, which is may be adjustable. FIG. 3 thus represents, in ordinate, the response on a logarithmic scale L, of the logarithmic converter 75 in terms of the level of gray G located in a range of N values, of a linear scale of predetermined gray, which extends from 0 to a maximum value Gm=N−1, with any one of these two end values representing the black. The logarithmic scale makes it possible to "expand" a first range of gray and to "compress" a second range. In the first range, which is expanded, the variations of the input gray levels will therefore be accentuated, thereby improving any insufficient contrast.

The logarithmic converter 75 may be formed on the basis of a logarithmic conversion table containing the value of the logarithm of each of the N values of the source range, or scale, of gray. It is however possible that the logarithmic conversion curve, which has a regularly decreasing local slope, traces an envelope curve which is close to the theoretical logarithmic conversion curve. In a case of this nature, the theoretical logarithmic conversion curve is replaced, as illustrated, by a series of segments which join points located at multiple whole levels of the same pitch in the logarithmic scale L.

Thus, by way of example, with the encoding source performed with 10 bits so that it goes from 0 to N−1=1023 gray levels, it may be provided that the three heavy-weight bits designate a range of gray levels G among 8 ranges in the logarithmic scale L given on the ordinate. The other bits, of low weights, are used for an interpolation, by specifying, in a linear fashion, the intermediate position of the G level being considered between the two extreme points of the range being considered.

Thus, FIG. 3 shows that the upper half of the range of gray levels G, starting with 512 on the abscissa, is encoded on only the upper section (3 heavy-weight bits: 111) of the logarithmic scale, i.e., ⅛ of the dynamic offered. In this way, the contrast is attenuated by a factor of 4. Conversely, the lower range, in which the three heavy-weight bits are at zero, i.e., the range in which the light-weight bits delineate the range from 0 to 7, representing 1/128 of the total range in abscissa, will also be represented by a segment representing ⅛ of the abscissa. It may thus be observed that the contrast is increased by a factor of 16. These two examples therefore show that the contrast yield of a source range may thus vary by a factor of 64 between the two ends of the range of sensitivity of the yield of shades of gray.

It will be noted that a logarithmic scale may be provided that is based on a base other than the binary base.

Figure 4:
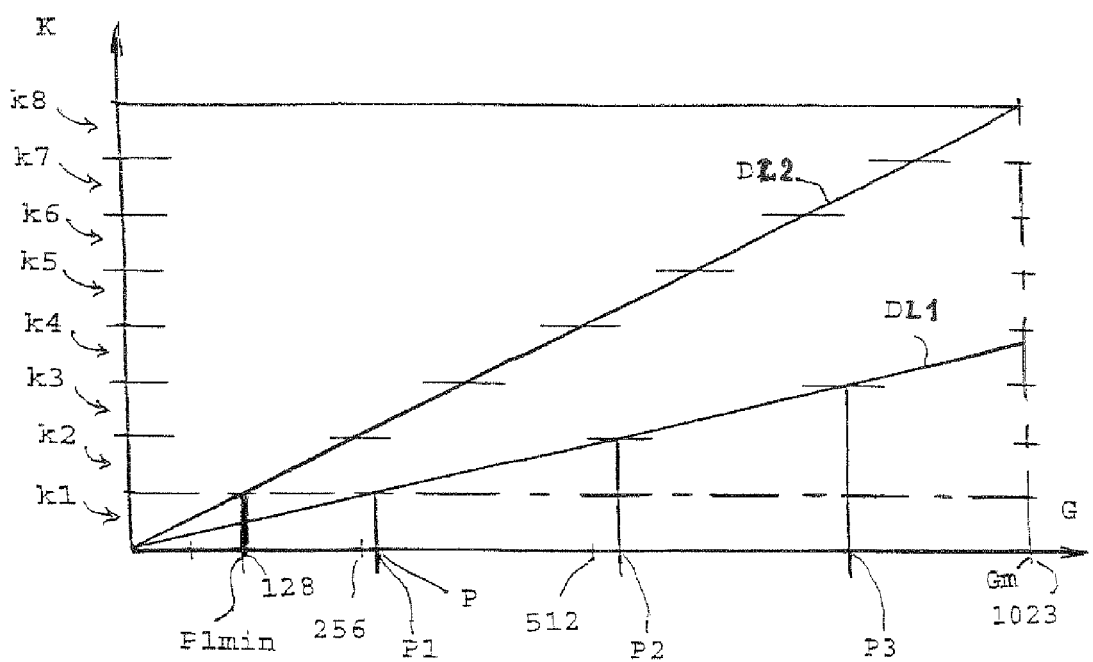
FIG. 4 illustrates a curve for converting levels of gray into various colors.

FIG. 4 illustrates the response of a code conversion block 76, which is controlled by a button 76B, and which converts the N gray levels G, illustrated on the abscissa, into elements with a given color which belongs to a predetermined corresponding color scale K, and which is illustrated on the ordinate. The above elements are elements which are directly visible, i.e., they are pixels, or data representing such pixels. In other words, the source range of gray levels G is cut up into a string of consecutive elementary ranges, each of which is distinct from the adjacent range(s) through a color that is unique to it from among a palette of colors available. The final image will therefore be striped into bands, each of which collects each of the pixel sources of gray levels G which differ only very lightly. Thus, two surfaces of a source image area which are only very slightly discernible from each other, because they exhibit gray levels that are somewhat similar, will now be better discernible since the difference in their gray level G is replaced by a difference of color, i.e., a difference in nature and no longer a difference in the degree of intensity. In particular, the outline of each line of separation between ranges will appear clearly, i.e., level, or equipotential, curves, which illustrate curves that are initially at the same level of gray. For example, a cylindrical surface of the object being examined (a tooth) will appear to be striated with color bands in the shape of an arc of a circle, clearly showing the relief.

In a minimal configuration, two colors are therefore sufficient to obtain the desired striped effect. In this context, it will be noted that the term "color" also includes the gray, since the aim is to highlight the equipotentials of gray level. An alternation can therefore be considered between unchanged bands of source image, therefore gray, and "colorized" image bands. We may also consider replacing the above colorized bands with the corresponding source image band, in which the gray levels are reversed with respect to an average, local level of gray of the elementary source range being considered. As an alternative of this last case, the above inversion may be provided as an absolute video inversion, i.e., with respect to a mid-point (here the value is 512) of the total source range. In this latter case, the lines of separation between final image bands are more visible.

The color yield of the various gray levels of a given elementary source range may be uniform, i.e., all the gray levels of the elementary source range will be rendered by the same intensity of the color being considered. This intensity may also be considered to be variable, one way or the other, in the gray level, which prevents a loss of information on the previous case.

In FIG. 4, correspondence between a current gray level G and a range of color having a rank sequence k is, to simplify this presentation, presumed to be linear and is represented by a straight line DL1 which goes through the point where the two scales intersect. The straight line DL1 cuts the upper limit of the lower band of colors k1 (k=1) in a point on the abscissa of value P1, and is therefore proportional to the inverse of the slope of straight line DL1. In this example, straight line DL1 completely cuts the three lower bands k1, k2, k3 and cuts the next one, which is the fourth, k4, partially. Button 76B therefore determines the slope of straight line DL1, or conversion sensitivity, by selecting the value of "increment step" P on a range which goes from 0 to Gm (exclusive), i.e., a value lower than Gm. For example, a maximum value of P1 which is just under Gm/2 (for example 511) makes use of at least the first two ranges of color k1, k2 possible.

Starting for example with a second multiple integer in the position of value P2, the code conversion block 76 then calculates the whole multiples of P1, which remain lower than Gm, returns to the straight line DL1 and deduces the upper limit of the second color band k2. In this example, since correspondence occurs through a straight line (DL1), the upper limit of the second color band k2 is therefore of an ordinate that is double the ordinate of the first color band k1, which can therefore be determined directly, simply by scaling. This simplification would however not be possible in the general case of a connection line with a non-geometric shape.

A button 76B, or any other element of man-machine interface, could be used to take a position of "wobulation", in which it controls an alternate scanning of a range of values by the pitch of progression P, therefore causing a variation of connection between each level of the scale of gray and the associated specified color, so that therefore the value of the width in gray levels G that each color band represents is made to "oscillate". Therefore, it follows that there is a modulation of the physical width, in accordion shape, of each color band on the image, and therefore an alternate displacement of the various image bands, whose limits, which can be upgraded in this way, will give a good illustration of the relief details of the tooth, which are rendered by a gray level in the initial image.

The above wobulation may be carried out by a sequencer which includes a counter that is used as electronic cursor, which is initially loaded to a selected value of the minimum increment size P, and which moves forward at the pace of a clock signal, until it reaches a value selected for the maximum "increment size" P. Typically, the counter consists of binary stages which can be divided by 2, which are cascade-connected, and which are therefore connected according to series propagation. FIG. 4 shows that it is thus possible, for example, to cause oscillation of the converting straight line between straight line DL1 and straight line DL2 if the increment size P varies continuously between values P1 and Pmin, where Pmin represents 128 because straight line DL2 is a diagonal line which passes through the eight color bands, namely k1, k2, k3, k4 and the following ones, k5, k6, k7 and k8.

A comparator compares the instantaneous value at the output of the counter to command a drop in the output of the counter, i.e., a reset to the minimum value when the maximum value is reached. This type of command may for example be enacted by registering the minimum value of the increment size P, through parallel access inlets to the various binary stages of the counter.

Once the circuits have been configured as a function of the user's commands, the code conversion block 76 that receives an image to be processed may then perform a comparison of the gray level G of each source value with respect to value P1 and its multiple integers, P2 and the subsequent ones, thus defining boundaries, in order to determine between which values of such bounds the current value is found, and may thus assign a corresponding color to it. This type of comparison may be performed using a table. It is also possible to place a count-down counter, which is initially programmed with the gray value of the pixel being considered, under the control of a clock signal time base of predetermined frequency, and in which a signal at sub-multiple frequency, which is precisely supplied by a divisor with value P1, controls a low-frequency counter. This low-frequency counter will thus provide the whole number being sought, which here is a multiple of rank sequence 3 (point of value P3) on FIG. 4, when the count-down counter will return to the zero state. It is therefore the fourth band which will be retained here for this source pixel.

Straight line DL2 shows that the choice of a smaller value P1 increases the slope, relative to straight line DL1, and therefore increases the number of color bands that are actually used.

The above cursor, which is used for wobulation, may be a visible element, i.e., a concrete member which moves on base 2, possibly along a graduated scale of position reference point, or else possibly a displayed image of such a cursor. However, the user may be able to detect the effect of his command to move the cursor only through the effect that this will induce on the recovery of the image, since it is this recovery, in color strata, which will influence the user to move the cursor in one direction or the other. The cursor may thus be limited to an electronic cursor, as indicated above, whose variable "position", which is encoded for a certain digital value, determines the positions of variable electronic pointers which trace the boundaries of various sections in the series of elementary ranges. The wobulation circuit cursor, which consists of a clock signal counter that is associated with control circuits used to cyclically count between two limit values, thus provides an upgradable value of an "increment size" for converting between the scale of gray levels and the scale of colors, so that the image is automatically animated.

The image processing circuits comprise a functional block 77 for smoothing out defects in the image, which is provided for measuring respective gray level values of nearby pixels in blocks of predetermined size, so that it is possible to determine a local reference gray level value, and to compare this value, in the case of a pixel with a gray level that has a variance that exceeds a threshold value relative to the reference value, then replace the gray level of the pixel processed with a replacement gray level that does not exceed the threshold value. Preferably, the replacement gray level represents a value of gray level that is an average of the pixels that are adjacent the processed pixel.

Thus, a point defect in the image that is caused by a parasite radiation received by a sensor, of CCD type or other types, will be attenuated, or even completely deleted, however a global treatment of the image will not modify the clarity of the areas of the image that have no defects. The process is therefore a targeted one.

The purpose of smoothing block 77 is therefore to eliminate, as well as possible, defects that are nearly point-shaped and which result from parasite radiations received by sensor 1. For this purpose, smoothing block 77 temporarily fixes the position of an analyzer window containing a basic box of, for example, 5×5 pixels. Calculating a mean value of the gray level G of the box, which is used as reference, makes it possible to detect pixels with abnormal gray level G. i.e., having, relative to the mean value, a deviation, or local gradient, whose absolute value exceeds a predetermined high threshold value. The above deviation may be is standardized by the mean value of gray level G, thus representing a percentage of variation.

If the absolute value of the deviation, or of the percentage, exceeds the value of the upper threshold, the gray level of the pixel(s) that is considered abnormal is then reduced to a value that is a function of the upper threshold, i.e., a value which deviates from the mean value, in plus or minus, by a quantity that is equal to the upper threshold or to a portion of this upper threshold. In order to better remove the fault, it is also possible to replace the gray value G of the, or of some of the, defective pixel(s) with a mean gray value, which is established using the gray levels G of the adjacent pixels.

Such a smoothing-out is done only in the defective areas of the image and therefore it does not introduce any fuzziness into the areas that are free of defects.

Programming of the above various subassemblies for processing images and managing sensor 1, can be provided as upgradable, by possibly downloading their software from an outside source, through PC 9 or directly by using radio circuits of base 2, in this case, of the portable telephone set type.

Processing unit 70 can therefore be functionally inserted into the link between memory 35 and microprocessor 31; in fact it can be substituted for the direct link illustrated, so that thereafter it transmits the processed image to PC 9. Memory 35 may however be provided with a size that is sufficient to store a large number of images, if needed, by being replaced with a mini hard disk. In other words, the functions of image processing and of medical record of the patients, which are provided in PC 9, may be provided in base 2.

Conversely, microprocessor 31 can receive still images from PC 9 and transmit them to processing unit 70 so that they can be displayed. This may involve images which were previously taken, or any other data, which could be alphanumeric. The practitioner may thus receive, for example, previous images taken in the medical record of the patient, in particular of his teeth, or he can receive other data which help him in his work. The images received may be standard images (pictures) or written text.

The digital link with PC 9 provides a pass bandwidth that is sufficient to allow the PC 9 to transmit animated images of predetermined throughput to base 2, the display screen 80 having the desired bandwidth. A channel of 64 kb/s makes it possible to receive animated images of "videoconference" quality, and the association of six such channels in parallel allows animated images of very good quality to be obtained.

Such animated images are, for example, images that originate from the outside, and which for example show a person speaking who is located in a help desk, and who is connected through the Internet 300 and PC 9, as is the case of server 400.

Conversely, base 2 may be provided with a mini-camera so that, in addition to the dental image taken during the examination, the local practitioner's image can also be taken and transmitted. Vocal circuits, such as microphones and speakers, may also be provided, to complete the video teleconferencing.

The digital link circuits may also be adapted to receive programming data of the base 2 from outside.

It is thus possible to initialize the software of the base 2 and thereafter to update it by downloading.

In other words, the base 2 may be prepared from a portable radio telephone, either cellular or satellite, provided with desired application software and required specific circuits, as indicated above, for managing image sensor 1, in particular its clock signals, and for processing the images taken.

In the case of a link that outputs the images taken towards an external means of processing, the base 2 thus constitutes, for the processing function provided by the external means of image processing, a front end which is temporarily substituted for the external means, during the phase of image acquisition.

The external link(s) may be corded or by radio, for example of the WiFi type.

Mechanical characteristics of the base 2 will now be described.

Casing 29 consists of a housing 29L, for receiving the image sensor 1 at rest, associated with a detector 29D of the presence of the image sensor 1, at rest in housing 29L, detector 29D which controls sleep/wake device 29V of the managing circuits of image sensor 1, in particular interface managing circuit 21 and circuit FPGA 33 as well as circuits 23, 24, 25. In this way, there is a reduction in power supply requirement, and in particular the battery discharge is limited, if a battery is involved.

Alternatively, housing 29L may be provided on the support base 100. The detector of presence 29D is additionally provided for controlling processor 31, which manages the base 2, digital link circuits 4, 5, 6 being however provided for at least partially awakening processor 31 in case data from the outside are received. The autonomy of a local battery is thus at a maximum, due to the fact that most of the circuits are on standby. When such data are received, they are received by the reviving circuit 31R, which controls the reviving of the desired circuits so that they can be processed and execute any instructions they contain, for example the reviving of all the circuits of the base 2. In such a case, reviving circuit 31R commands sleep/wake device 29V to change its status at the output to instruct the control circuits to revive.

The presence detector 29D may be a mechanical switch which is controlled by sensor 1 and which presses the switch when it is located in housing 29L. Alternatively, an optical transceiver is provided, which is of the electroluminescent diode type, and an adjacent optocoupler receiver, and sensor 1 serves as a reflector so that it sends a ray, emitted by the diode, back towards the receiver. The optocoupler's standard output transistor therefore becomes conductive and can thus provide a digital level "0" which is applied at respective standby inputs of the various circuits involved, for putting the same on stand-by. The sleep/wake device 29V provided here is therefore only optional during this phase. However, the sleep/wake device 29V allows the reviving circuit 31R to control an inhibition of the standby function. For this purpose, the sleep/wake device 29V is here a logic gate of the OR type with two inputs, one of the inputs being controlled by the output of the above-mentioned optocoupler receiver and the other input being controlled by the reviving circuit 31R. The inhibition command issued by reviving circuit 31R is therefore a move into status "1", which therefore forces this status "1" towards the output, independently of the status of the other input, and thus initiates revival. It will be noted that the above standby and revival circuits could also be incorporated in a base which has no display 80.

Interface managing circuit 21 is adapted to recognize a type of sensor 1 from among many possible types in memory, and also to recognize the size of sensor 1 from among many, in memory, so that it can perform the corresponding management. Base 2 is thus universal. Recognition of the type and size of sensor 1 takes place through the content of a mini-cassette which the user inserts into interface managing circuit 21. However, each type and size of sensor 1 may be provided so that they are characterized by the specific wiring of certain pins of connector 12C of cord 12 which is linked to connector 20, the latter being connected to interface managing circuit 21. This specific wiring may consist of by-pass links between pins on connector 12C reserved for this purpose and which thus provide a logic level 0 or a logic level 1 for the pins that are electrically "in the air" (not driven), and which might be polarized with a pulling resistance at logic level 1. The various pins above thus provide addressing bits for various sections of a memory 21M in the interface managing circuit 21, said bits containing the controls and the processing mode for the various types and sizes of sensor 1.

The base 2 additionally comprises a housing for a battery which feeds a power supply that provides the desired voltages for base 2 and sensor 1.

The adapter module 6 includes a sequencer of general architecture which here is similar to that of sequencer 32, with a time-based managing microprocessor that has a DSP processor, a programmable slave circuit FPGA that is paced by an oscillator and which controls a RAM memory processed in FIFO. As indicated, the adapter module 6 connects the radio circuits 5, which here are incorporated into the adapter module 6, to the corded port 91, where this link is made using a linking interface circuit, which here is of the type USB, and is connected to corded port 91. Module 6 may be included as a board inserted into an internal connector in PC 9.

Link 13 transmits the image data, as well as processing control data originating from base 2, to PC 9. Link 13, with the corded link that constitutes an extension thereof, is however bidirectional, so as to allow PC 9 to control, if needed, certain functions of the base 2.

Processing PC 9 comprises software for processing received images, i.e., for filing them in a library (described below) of medical records Dp of patients, which could be consulted later by calling upon the specific address desired. PC 9 here comprises downloading circuits 92, in contact with server 400 connected to the Internet 300, provided for receiving and recording files of updated software for image taking or processing, or even files of image records of patients. The files may also be locally received by means of a removable data support such as a diskette. The downloading circuits 92 can access port 91 through a microprocessor in PC 9, in such manner as to transmit all updates to base 2. This may for example involve software that is intended to be stored, in whole or in part, in the programmable circuit 33, with possible previous adaptation by the microprocessor 31, this software allowing for example someone to use a sensor 1 of another type, which therefore requires other sequencing signals. Memory 21M, for specification of sensor 1, may also be connected to the programmable circuit 33, for the same purpose.

As mentioned above, all or a some of the functions of PC 9 may be incorporated into base 2. Moreover, the digital link circuits 4, 5, 6 here are arranged to control the switching of image data towards one of among a plurality of external systems for processing the image, i.e., PC 9 or any other system. For this purpose, PC 9 may for example be used as a point of access to a local or wide area-data transmission network, for example Internet 300. The practitioner can thus transmit the image to any desired PC in his office or he may also transmit the image to a PC at a remote site, connected by means of a data transmission network, for example, the Public Switched Telecommunication Network (PSTN) or the Internet.

Alternatively, the radio link portion 13 may be replaced by a radio link in a cellular or satellite telephone network. Base 2 may in particular consist of a cellular phone station into which the software for the desired imaging functions, as described above, will have been incorporated. If needed, for the interface with sensor 1, circuits operating at specific electrical levels may be added, for example for the clock signals. To maintain the normal casing of the cellular telephone, and therefore to limit costs, this type of specific hardware may be incorporated into an additional adapter casing, which is connected to a standard port provided at the bottom of the cellular telephone's casing.

In this example, base 2 includes voice input control circuits, in the form of a microphone 27 (FIG. 2) whose output is connected to sampling and scanning circuits 28, which may in fact be part of the DSP circuits 31S. The DSP 31S includes voice recognition software, i.e., spectral analysis circuits associated with a library of reference control words to be recognized, for, inter alia, controlling a switch that functions as an activation button, which can therefore be omitted. The practitioner may also control PC 9 in this manner, in order to activate the desired software for image storage and consultation of old images in storage in PC 9 or in the remote server 400. In a similar remote consultation case, there is also activation of software for used to set up the desired Internet link, which utilizes downloading circuits 92. A switch may also be provided to activate the source of the X-rays. Alternatively, voice recognition may be performed in processor DSP of PC 9, by transmitting samples of voice signals to it.

Figure 5:
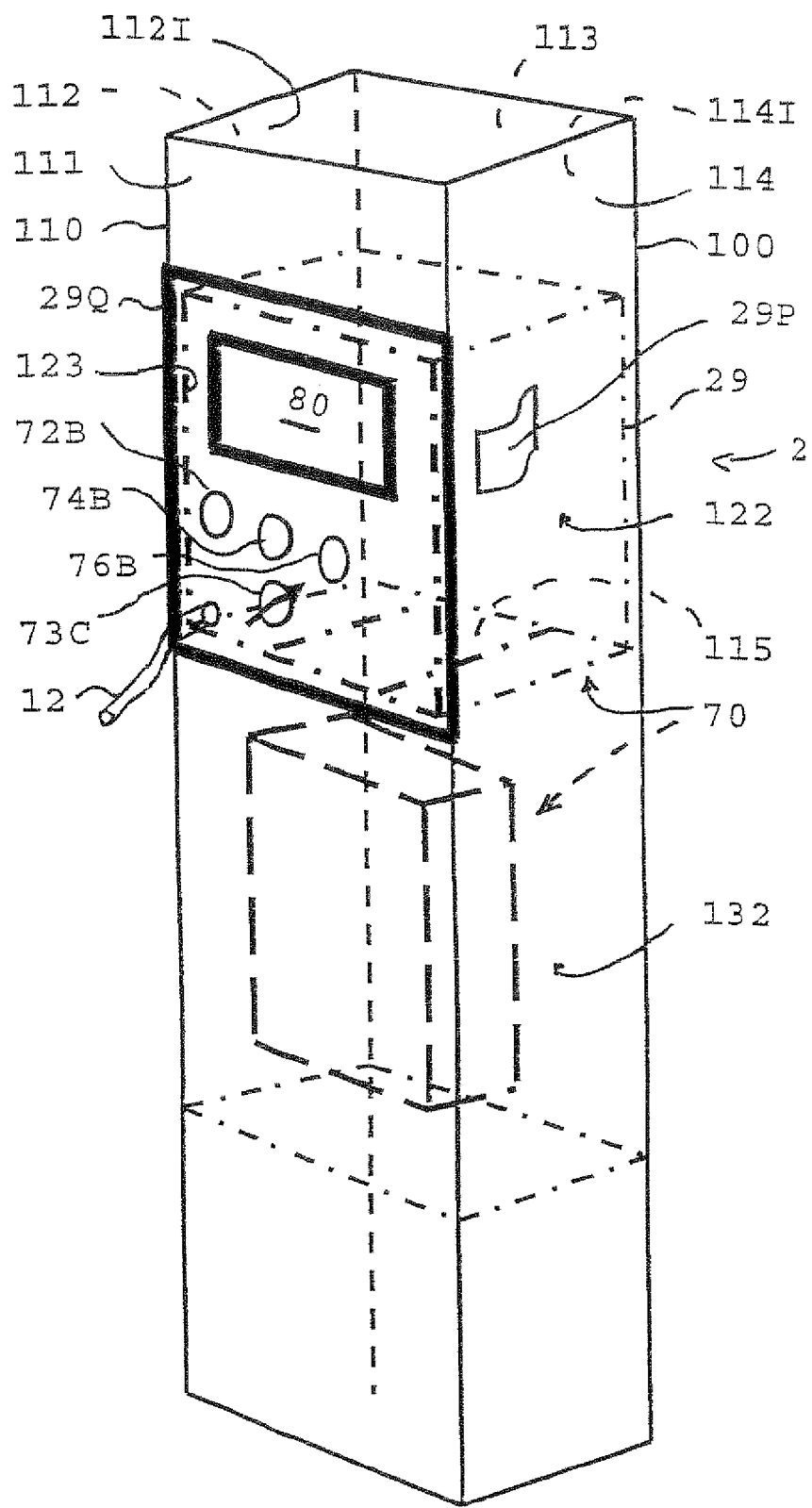
FIG. 5 is a perspective view of a support arm for a source of X-rays, which is used as a casing for the base.

According to the second aspect, as shown in FIG. 5, the support base 100 which supports base 2 may be part of a support arm 110 for a source of X-rays, whose radiation it detects through a said sensor 1 connected by cable 12. Arm 110 may, on its exterior, feature casing 29 or, as in the present case, constitute an enclosure for casing 20 or it may even itself constitute such a casing 29.

To this end, arm 110 is here a tubular beam of square transverse cross-section, about 5 cm on each side, made of aluminum, with said beam provided with a housing 122 for casing 29. One, 111, of four lateral walls 111, 112, 113, 114 (in that order) of arm 110 includes a window 123 for a front plate 29Q or frame to be placed inside it, for carrying man-machine interface components, i.e., the display 80 screen, buttons 72B, 74B, 76B and cursor 73C, and all the other subsidiary buttons and indicators, the housing of sensor 29L (not illustrated) and the corresponding end of the cable 12 being also accessible. The remaining part of the base 2, i.e., essentially the electronic-circuit processing unit 70, is here located behind the screen of the display 80. For ease of the description, the arm 110 is presumed to be vertical.

Casing 29, whose size is substantially identical to the size of housing 122, is introduced therein through window 123, until it rests against the, opposite, lateral wall 113. A horizontal leg 115, defining a transverse slide, supports casing 29 in the lower part of housing 122. To keep it well in place, casing 29 includes at least one tongue or elastic leg 29P, or two of them being laterally opposite, only one being illustrated, resting on the internal surface 112I, 114I of the two lateral walls 112, 114 which define window 123. Tongues 29P thus ensure the maintaining in position through the coefficient of friction, on the two internal surfaces 112I, 114I of aluminum. It is however possible that the two internal surfaces 112I, 114I each comprise a small relief, so as to constitute a catch. In a dual manner, the tongues 29P may be provided on the internal surfaces 112I, 114I. Alternatively, the two tongues 29P may be replaced by a same tongue, which could be single, and which rests on a horizontal leg which limits the upper part of housing 122.

In another alternative, the support leg 115 is replaced by two ribs or horizontal grooves located in the internal surfaces 112I and 114I and cooperating with two grooves or ribs of casing 29 respectively.

In still another alternative, illustrated for convenience in this same FIG. 5, support leg 115 is omitted and housing 122 is vertically extended, here downwardly, by means of a housing 132. In a corresponding manner, the base 2 has a more elongated shape, i.e., all the electronic circuits of the processing unit 70 constitute a mechanically separated module, essentially located in the extension, here inferior, of the screen of display 80 and here connected to this screen, and to the elements of the front plate 29Q, by means of flexible wires, not illustrated, for example ribbon cables. The base 2 thus consists of two mutually movable parts, namely, on the one hand, front plate 29Q with its elements of man-machine relations and, on the other hand, essentially the electronic-circuit processing unit 70.

The portion in consideration of the arm 110 thus constitutes some kind of vertical shoe which constitutes casing 29. The module of the electronic-circuit processing unit 70 is thus protected against shocks, and it is sufficient that the internal walls of arm 110, or the above module, carry an insulating layer to prevent any risk of electrical fault. To overcome the necessity of having an insulating layer, it is possible that a printed circuit card which carries the electronic-circuit processing unit 70 comprises radial legs which serve as crosspieces with respect to the four internal surfaces of the arm 110. The assembly is achieved by obliquely sliding electronic-circuit processing unit 70 through window 123 so that they then pivot towards a position of vertical extension, front plate 29Q then being brought into desired position in window 123.

Due to the fact that, in this embodiment, the center of gravity of the whole of the base 2 is lowered, and electronic-circuit processing unit 70 is captured by gravity inside the blind housing 132, there is no risk that casing 25 will fall out of housings 122, 132. It is sufficient, for example, that front plate 29Q remains at the bottom of a small gutter provided at the level of the lower edge of window 123, to have a stable position. Indeed, since display 80 and electronic-circuit processing unit 70 are hooked behind front plate 29Q, their weight exerts a restoring torque on the front plate 29Q by rearward tipping, pinning its edges on the edges of window 123, which is more narrow, said torque being opposed against any parasite vibration which would tend to cause front plate 29 to tip forward.

The interest of such a "sock"/"booth" assembly resides in the fact that the whole volume of the arm 110 is readily available to place therein a said electronic-circuit processing unit 70 possibly more massive than in the present description. In addition, arm 110 constitutes a Faraday-type electromagnetic screen, which protects electronic-circuit processing unit 70.

Figure 6:
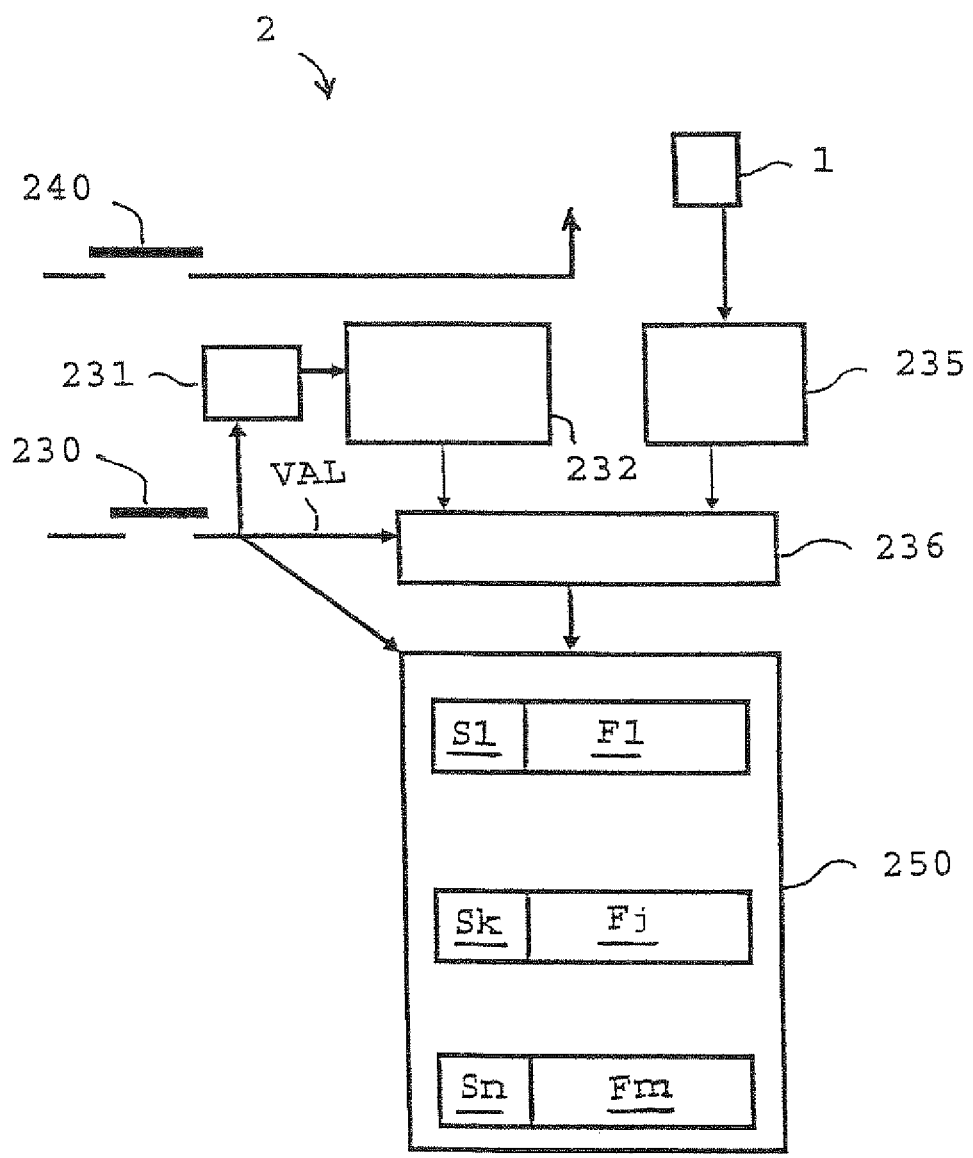
FIG. 6 is a schematic view that illustrates a system for taking dental images, including the above base as well as a library for filing sequences of images representing the series of teeth of a patient, with said images being classified in the natural order of the position of the teeth in each row.

According to the third aspect, FIG. 6 is a block diagram which represents, very schematically, in base 2 for which, once again, none of the above elements have been illustrated, sequencer circuits for filing a sequence of images of the series of teeth of a patient, in an electronic library.

First of all, the technical goal and the purpose of achieving this goal are described below.

When a practitioner examines a patient, the current practice, at least in certain countries, is to draw up a complete "inventory", i.e., take a sequence of images that correspond to the series of teeth of the lower and upper jaws.

In order to facilitate the processing of the series of files of dental images thus obtained, it is therefore necessary for each file to be assigned reference points, using position data within the sequence; these rank sequence data provide identification for the tooth being considered.

It will be understood that in the following FIGS. 6 and 7, for clarity of the present presentation, the functional elements that are illustrated are very schematic, i.e., for example, microprocessor 31 and the associated circuits can provide the additional functions described herein. In this case, each functional element illustrated consists of microprocessor 31 and the associated circuits with, in addition, memory circuits containing the software for application of the desired sequencing. Thus, the "concrete" embodiments, as disclosed herein, correspond to the first said type, but they may also be produced using software, according to the second type.

FIG. 6 illustrates a first embodiment, which makes it possible to achieve this goal. We can see that, when the source of X-rays has been activated by an image-taking button 240, which may possibly be incorporated into a keyboard on base 2 and be connected to said source with a link, preferably a wireless link, the electronic image that is captured by the sensor 1 is transmitted to a buffer memory 235, which is equivalent to memory 35, and the image is thereafter filed in a library 250, through a transfer circuit 236.

Transfer to library 250 is controlled by a validation button 230, which is part of base 2's keyboard, and which provides a VAL signal, for validation of the image being examined, on the screen of display unit 80 (FIG. 2). The VAL validation signal unlocks transfer circuit 236, so that the image file under examination is transmitted to library 250, where the VAL signal furthermore induces a corresponding writing command in library 250, so that the presence of a lock for the transfer circuit is only optional, and this circuit is here presented only for educational purposes. On the other hand, transfer circuit 236 also transmits counting data of the images taken, with said counting data coming from the output of an incremental image counter 232, which can be designated as ordinal, since it indicates the rank sequence j of the image file Fj in the sequence.

Buttons 230 and 240 may be replaced by any man-machine interface, for example a mouse or a touch screen consisting of the screen of display unit 80, or even, preferably, a voice recognition system, which may be relatively simple since the number of commands to be recognized is very limited.

FIG. 6 shows that the incremental counter 232 will move forward by one step whenever the validation button 230 will be activated, i.e. when the VAL validation signal signals a clock input to counter 232, which is however through a delay circuit 231, which delays a corresponding progress signal which is sufficiently long for the number k, at the output of counter 232, to be read by the library 250, before it is incremented into a number k+1, therefore with a certain delay, or time phase difference. The delay circuit 231 consists for example of a low-pass filter, with series resistance, which feeds a first electrode of a capacitor in which a second electrode is polarized at a fixed voltage, for example by means of a ground or a supply voltage. The first electrode is preferably connected to a reformatting circuit, for example a hysteresis logic circuit, known as the Schmitt trigger, which restores sufficient stiffness to a switching edge signal, to allow it to activate the clock input of counter 232.

Alternatively, delay circuit 231 is left out. Writing in library 250 is activated by a front edge of the VAL signal and counter 232 is arranged so that it then advances when the VAL signal has a rear edge (which may be a rising or descending edge), which appears when validation button 230 is released. In the embodiment, in order to dispense with the length of time that validation button 230 is activated, and with any bouncing it may experience, validation button 230 may for example signal the activation of a monostable (one-shot) circuit, which is the equivalent of delay circuit 231, thus providing said front edge, and where the edge activates the writing of data into library 250, and a rear edge, the disabling edge, which causes counter 232 to move forward with the desired phase shift. Preferably, the monostable circuit is of the non-rearmable type (once it has been enabled), i.e., it provides a pulse of a predetermined length of time, even if validation button 230 remains activated for a length of time which exceeds the pulse length of the monostable, one-shot, circuit.

It will be noted that counter 232 could, alternatively, operate as a down-counter starting with a predetermined number, because it involves establishing a specified series of "m" numbers, and the fact that these numbers are consecutive or even that this series is increasing or decreasing has no importance. Thus, in general, counter 232 may be replaced by any circuit that generates a sequence of numbers which are mutually independent and are all different, so long as library 250 is read using a generating circuit of the same type, i.e., one that has the same progression algorithm.

Image file Fj of rank sequence j (where j varies from 1 to m) that was just written in library 250 forms a block of useful data, which is associated with a block of service data Sj, which comprises an order number that represents the digital rank of image file Fj in the sequence of "m" files. This association of the two blocks of data Fj, Sj constituted in this way may be physical, therefore with the image file Fj and the service data Sj, containing the order number j, the two blocks being stored together in a memory area that is reserved for them, consisting of elementary memories with consecutive elementary addresses. Alternatively, the two blocks are disconnected and one of the two blocks in the pair Fj, Sj may include indirect addressing data from the other block.

If the image currently being examined is of unacceptable quality, the practitioner does not activate validation button 230 and he signals that a homologous image be taken, i.e., he holds sensor 1 behind the same tooth. The file of the defective image is therefore overwritten, in the buffer memory 235, by the new image file, and the operation may be repeated as desired. Counter 232 therefore remains in phase with the number of validated images, since it is solely the series of validation signals VAL that causes the counter to move forward.

Library 250 is thus progressively filled with a sequence consisting of "m" image files F1, ... Fj, ... Fm, each being associated with the block of service data S1, ... Sj, ... Sm which specifies its position or rank sequence j in the sequence.

Alternatively, means may be provided for systematically writing all the image files Fj in library 250, whether they are good or bad, and in this case, it will be the service data Sj which will specify, during a later reading, which is the image file Fj should be processed among many image files Fj of same rank sequence j, each being associated with said service data Sj.

During reading, in order to remove ambiguity with respect to validity, it is possible to read time-stamped data associated with each image file Fj, so that only the most recent of those of the same rank sequence j is retained. The interest of such a solution is that it requires no specific writing, since, typically, all the files are automatically time-stamped by the operating system, which is part of the sequencer circuits. Alternatively, arrangements may nevertheless be made for supplying, in the service data Sj, a copy of the VAL validation signal, which will explicitly designate the image file Fj that is valid from among those of the same rank sequence j.

According to yet another alternative, it may however be possible for library 250 to be used, at least for writing, as though it were a shift register, i.e., the library 250 acts as a conveyor, with a single point of data input on a current lead-in area. The various image data blocks Fj are then conveyed while maintaining their order of ingress, i.e., by forming a string, without branching out towards various memory areas. In other words, there is no so-called random addressing; addressing in writing is predetermined, i.e., on a series of specified memory areas. It will however be understood that this involves logic management of the various areas, which means that nothing, physically in the addressing plan, prevents the areas from being adjacent. All that is required is that, at all times, there be a predetermined pointing logic link pointed towards the following or preceding area.

If, however, the addresses of the consecutive memory areas are joined and together they define a memory area with a known length (number of elementary addresses in the area), the service data S1, . . . Sj, . . . Sm may then be omitted, since the address "increment" size from one image to the next one in the series is known. The first image file F1 may comprise a flag that makes it possible later on, when reading it, to tag the start of the sequence of files, in order to count, from there, any desired number j of "increments" in order to access a read-only file of a certain rank sequence j.

As indicated above, the serial input library 250 may be of the serial output type, which means that it may be of the FIFO type. It may also be specified that it is to be addressable at will for reading, i.e., of the RAM type. It will be noted that a RAM memory may be processed as a serial input memory, i.e., by addressing, in writing, and using a sequential counter of the type used for counter 232. The above sequential counter controls, in an alternative manner, the addressing of the RAM memory through the input channel of a two-channel parallel multiplexer, in which the second channel, which controls addressing for reading, receives the output of a register supplying random addresses, i.e., addresses defined at will by the user, through the electronic circuits (microprocessor 31 and others) controlled by it. The status of a writing or reading control bit in the RAM memory also controls the desired switching of the multiplexer, for selecting a suitable addressing control channel.

Figure 7:
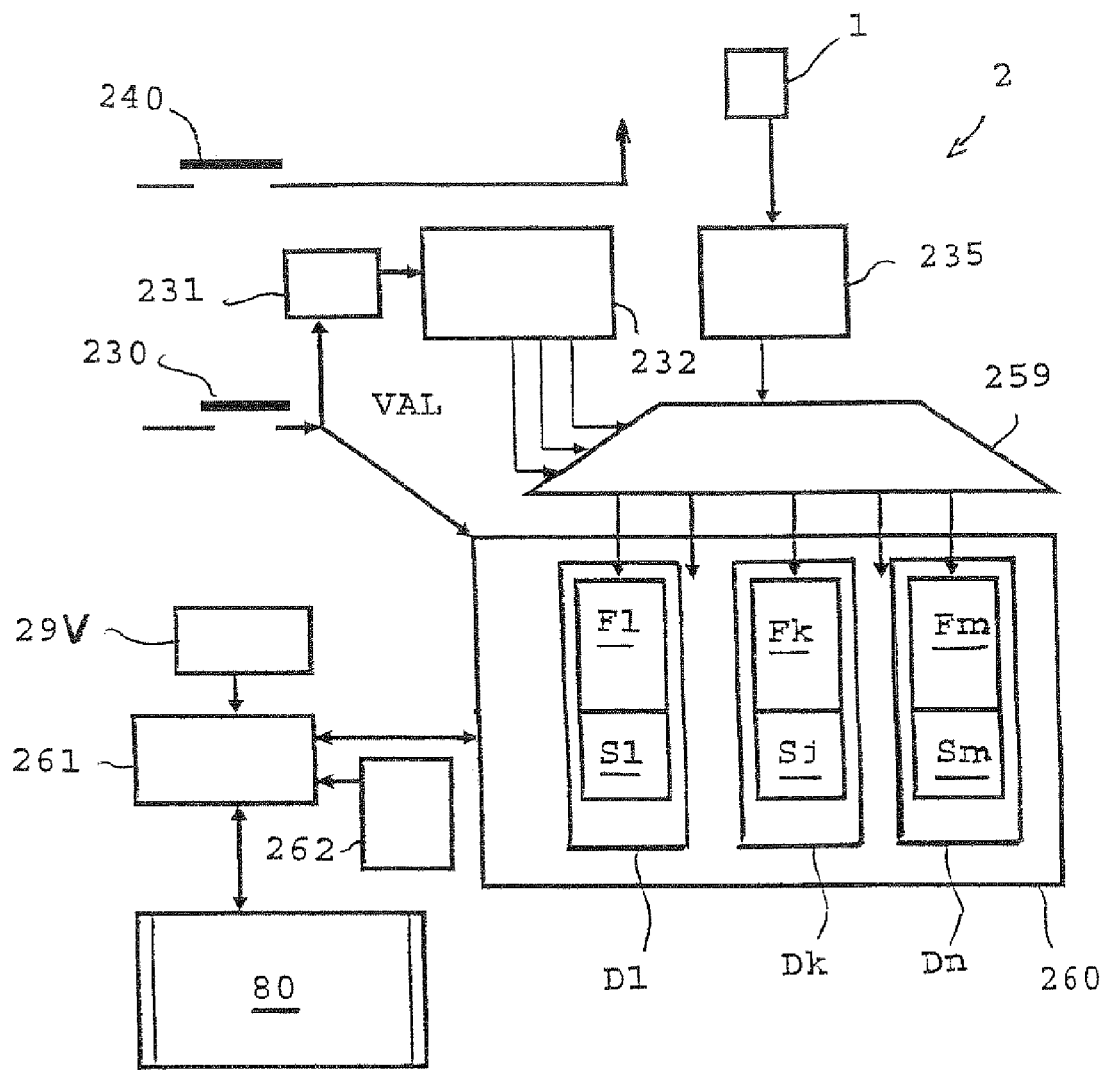
FIG. 7 illustrates an alternative of the system in FIG. 6.

FIG. 7 is an alternative of FIG. 6, in which library 250 is replaced by a library 260. Contrary to the alternative (series) of library 250, library 260 is of the parallel access type, i.e., of the so-called random type. Library 260 thus consists of a plurality of at least "m" memory areas which can be accessed in parallel, at least where writing is concerned, through a switching circuit consisting of a demultiplexer 259 with "m" output channels, thereby connecting the output of the buffer memory 236 to the desired memory area. The parallel outputs of counter 232, which provide the rank sequence j of the current image file Fj, are here applied to addressing control parallel inputs of demultiplexer 259. In this way, the outputs of demultiplexer 259 are successively activated each time a validated image file is received, so that, when a sequence of images is taken, a scanning wobulation of the successive memory areas is performed in writing, by writing therein, each time, the file Fj being considered.

It will be noted that the relative physical positions of the various memory areas may be freely chosen, i.e., they may be mixed and tangled up in any order, as long as the reading circuits have been provided so that demultiplexer 259 can be used in the same way, and they will therefore be used as a "descrambler" of addresses.

Here again, since the Fj files are filed in a specific order, the data for indicating rank sequence j in the service data S1, . . . Sj, . . . Sm may be omitted, since the address of each image file Fj corresponds objectively to its rank sequence j.

We can see here that it is the validation signal VAL that controls writing in library 260, which means that non-validated files presented at the input of the library 260 by demultiplexer 259 will not be recognized.

Alternatively, however, and as in the case of FIG. 6, each memory area of library 260 may be "doubled" by one or more similar areas, so that a plurality of image files Fj having the same rank sequence j may be stored. Sorting of the image files Fj, for reading the validated image file Fj, is performed as indicated above.

In these various examples, the buffer memory 235 may in fact consist of a current area of library 250, 260, which means that the image file Fj, while it is being examined, will immediately be written into library 250, 260, and that it will then be validated or not. As indicated above, the image file may be overwritten by a new image file Fj of the same rank sequence j, or it may be marked as invalid, with this indication being explicit or possibly implicit, if explicit validation data is absent.

The invalidation control circuits may also be adapted to associate service data to the image data to be transmitted, using external processing means, which specify that the image is invalid. In particular, an image file Fj may be inhibited by giving it a rank sequence that is outside the range of sequence which varies between 1 and m. In other words, the file is not destroyed by a specific destructive action, however it is switched towards a non-existing or unused memory area, so that the final result, inhibition, is still the same.

For example, counter 232 will include, at its output, a quenching circuit that has a predetermined status, for example an inhibition circuit for any positive address output, which thus fixes, at the output, an address of rank sequence j=0. In such a case, the address of rank sequence j=0 will not be recognized by library 260, so that there will be no writing of the image file F, or else the address of rank sequence j=0 will correspond to a trash can area.

Deletion of the image may therefore be handled by base 2 or else it may also be remotely controlled by the base 2 in its processing unit.

It will be noted that library 250, 260 may be located in the base 2 or may be remote, for example it may be in the local PC 9, or in a remote server.

Thus, we can see that the practitioner does not have to manage the filing of consecutive image files Fj, since it is the sequencer that handles this managing task as a function of validation signal VAL. The validation signal VAL may be automatically produced using an interval timer after a certain delay, after obtaining the current image file Fj. A burst of at least two activations of the image-taking button 240 within a specified short time lag, for example 1 second, may also be used to cause a single image to be taken, which means that it is not interpreted, thanks to a low-pass filter towards the source of X rays, as being a plurality of controls for taking images, however this burst also generates the validation signal VAL. In such a case, after taking one image, the first validation signal VAL will have to be considered as being a single flag at the start of a sequence, since no image will have been taken until then. The above interval timer will allow validation of the last image file Fm in the sequence, since the practitioner, once he has stopped taking images, will not cause the necessary last validation signal VAL to be supplied.

The interval timer may be placed on standby, to permit any setback to be tolerated which would prevent the practitioner from examining the current image within the desired time period.

To simplify the practitioner's task, the sleep/wake device 29V is also provided here for activating a managing function for the electronic medical files that constitute the patients' client files D1, Dp, Dq, each client file Dp being filed in a memory area consisting of an identifier such as the name of the patient, an intervention history and the dental image files Pj, all this information being shown on the display unit 80, preferably with the images in sequence. All the client files Dp are kept in a memory defining an electronic library, remotely located, for example in PC 9, or else, as is the case here, in base 2, which means that library 260, or 250, constitutes a global library for the client files Dp.

While sensor 1 is being "disengaged" from housing 29L, the sleep/wake device 29V activates the managing function of the above sequencer circuits, for taking dental images, and activates the above managing function, specifically of the addressing and managing circuits 261 of the client files Dp. The desired client file Dp for a patient is automatically selected, as will be explained later, or manually selected using a man-machine interface, for example keyboard 93 of PC 9 or, as is the case here, the keyboard of the base 2, or even by means of a touch screen, which here is the screen of display unit 80. In particular, for selection purposes, file library 260 is here associated with an electronic agenda 262 which includes a list of client patients scheduled for each day, as well as the corresponding time blocks. Agenda 262 appears on display unit 80 whenever the sleep/wake device 29V is activated and the practitioner may then use his finger to point to the desired time block, which appears on the touch screen of display unit 80.

In order for the selection to be completely automatic, circuits 261 that manage the directory and library 260 provide a sequential presentation of the client files Dp, which are respectively associated with consecutive time blocks, at each activation of the sleep/wake device 29V, so that the practitioner does not have to intervene to select the client file Dp of the patient being examined. This therefore involves "auto-dial on pickup", i.e., an automatic activation of the reading function of the client files Dp, with an automatic addressing of the desired client file Dp, i.e., the client file Dp with the appropriate rank sequence. Only the arrival of an unexpected additional patient or the absence of a scheduled patient will require the practitioner's intervention, in order to update the list. Alternatively, the time base 30, and not the sleep/wake device 29V, which controls the selection of the next client file Dp+1.

Once the desired client file Dp has been made accessible for reading and writing, the practitioner may then, by using only the touch screen of display unit 80, call to the screen any desired information concerning a patient's history and write in the Dp file to update the history, by writing a description of the care that has just been provided, by touching specific areas of the touch screen, which functionally constitutes a keyboard. In the case where a limited number of dental images are taken, the practitioner may in particular use his finger, on the touch screen of display unit 80, to point to the image of the tooth being considered, in a row of slots which represent the jaw being considered.

In order to limit the volume of the equipment, the content of library 250 or 260 may be transferred every evening to a mass storage unit of the PC 9 or to a remote server, and, conversely, the day's client files Dp will be written in it, which means that library 250 or 260 serves as an immediate-access buffer.

Figure 8:
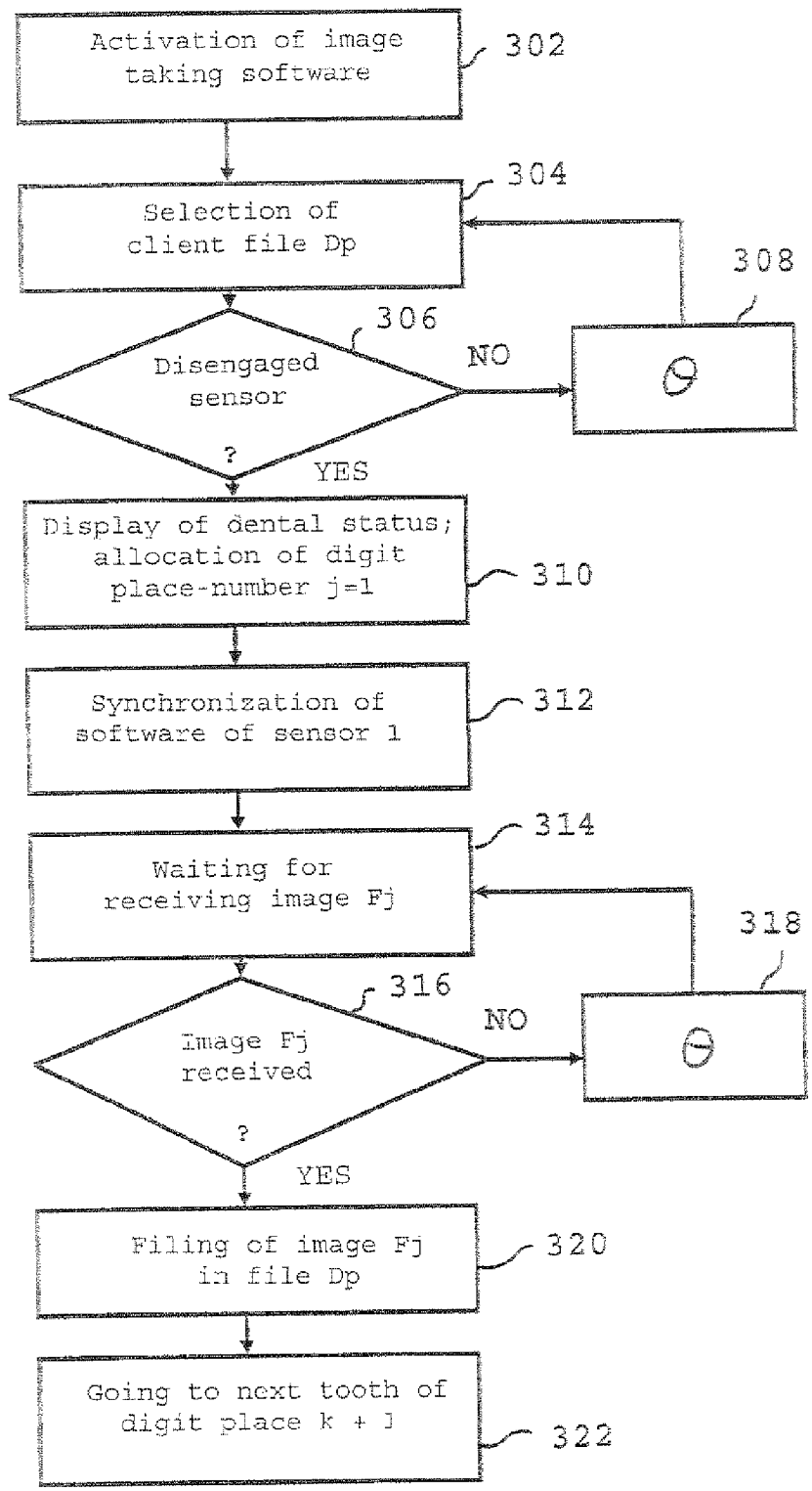
FIG. 8 is a flowchart that illustrates management software, which manages man-machine relations for using the above system, and which ensures that the execution of the image-taking sequences will be under the practitioner's control.

FIG. 8 is a flowchart which illustrates a mode of utilization of the system, as managed by a software called PIM, for Picture IMaging, (FIG. 1), for taking and displaying images. The PIM software manages the circuits disclosed above. It will however be understood that some of these circuits may be replaced by a series of instructions for the PIM software, which provides a desired operation.

When a step 302 is reached, the user activates the PIM software, by selecting an icon on screen 90 of PC 9. Alternatively, this activation may be performed by pointing to an icon on the touch screen of display unit 80, if the latter is kept active with respect to at least its information input function. PC 9 therefore addresses a memory area thereof, which contains instructions for PIM software. Since the dental images taken by the base 2 are, in this example, finally returned to PC 9, here, as time goes by, the PIM software is installed so that it is shared between PC 9 and the base 2, in the form of a PIM9 software and a PIM2 software respectively, each of which is locally installed (FIG. 1). It would, however, be possible to consider storing all the global PIM software, in just one of the above two managing elements, i.e., PC 9 or else in the base 2, and, in such a case, the element which has no PIM software, i.e., the base 2 or PC 9, would read the desired instructions in the other element, i.e., PC 9 or the base 2 respectively.

The above activation of PIM software causes the display, on screen 90 of PC 9, of a home page that allows the user to choose one said client file Dp, in a step 304. Selection of the desired client file Dp takes place by pointing on screen 90 of PC 9 or else is carried out automatically using PIM 9 software from the client list, that is to say, the patients to be expected as indicated in the agenda.

The various man-machine interface controls may be enacted by pointing on screen 90 of PC 9, by input with keyboard 93 of PC 9 or by voice control. All these controls may also be input using base 2 to signal the latter, or to signal PC 9 through the link which connects them.

At least one of screen 90 of PC 9 and the screen of display unit 80 then displays a civil status chart, which specifies the characteristics of the patient in question, i.e. his name and his address, the dates of previous interventions, if any, and other useful information. A dental status is also displayed which consists of dental images previously taken, i.e. images from image files Fj, for example the sequence of image files Fj which were stored during the last intervention by the practitioner. The latter may signal a rollback of the series of sequences of image files Fj established during consecutive interventions and which constitute a history. At the level of the base 2, whose screen of display unit 80 is of limited size, the practitioner may order the display of a limited number of tooth images in the selected sequence, thereby constituting a dental status of limited size. The teeth images are tagged with a number which corresponds to an international norm or a norm of the United States of America.

In a step 306, for status polling, the PIM software tests the state of detector 29D for the presence of image sensor 1 in housing 29L, i.e. it tests for the possible existence of a disengagement state of image sensor 1, and if this is not the case, branch NO, i.e. if detector 29D gives a non-detection signal, the path goes through a loop-back step 308 with a pause (shown schematically by symbol θ) of a predetermined duration, towards status polling step 306. This looping back operation is cyclically repeated, up to an output through a branch YES, where the existence of the disengagement state is detected. The awakening of the desired circuits, through the sleep/wake device 29V for the managing circuits of image sensor 1, is thus controlled by detector 29D, either directly or by means of PIM software. A man-machine interface control may be provided, for example the activation of an area of the touch screen of display unit 80, which replaces the detection of the disengagement state of the polling step 306.

Branch YES leads to a step 310, in which an empty dental status is displayed, i.e. a pattern of empty slots, each of which is tagged with a specific tooth number, depending on the desired norm. In the corresponding sequence of the above numbers, PIM software addresses the slot of a first number of the sequence, i.e. it will file, in the corresponding memory area, the first image, F1, that will be taken, to which it will therefore have assigned the first number. The practitioner may however give instruction to go directly to the taking of an image of rank j>1, i.e. not to input a certain number of images of the beginning of a sequence. He may even cut off the end of the sequence.

It will be understood that the number of each image in the sequence may be arbitrary, i.e. the image numbers are not necessarily consecutive numbers, since the only two constraints are that the PIM software associates an identifier for each image and that the PIM software browses through the sequence in a predetermined order.

In a next step 312, the PIM software performs software synchronization between the PIM9 software of PC 9 and the PIM2 software of the base 2. For this synchronization, the PIM9 software controls the PIM2 software for, if necessary, awaking microprocessor 31 and the associated circuits, and also so that the PIM2 software to can activate a subprogram for receiving an image taken by the image sensor 1. The base 2 will then generate, for the practitioner, a signal indicating that it is ready to take an image, with this signal being for example an alert sound, in the form of a beep, or this signal may be visual. The practitioner can therefore place the image sensor 1 in the mouth of the patient and activate the X-ray source.

As has been revealed above, during a step 314 for waiting for and receiving an image, the image which is taken is stored in the base 2 and is displayed therein, precisely in the selected slot of the dental status, i.e. the first one, unless there is a command to the contrary. The practitioner may, as indicated above, cancel the image taken or process the image. The screen of display unit 80 additionally displays the last dental status, i.e. the old image of the same tooth taken on the occasion of a preceding intervention, so that the practitioner may easily see the progress in the condition of the tooth. The PIM software may also perform an operation which compares the above two images Fj. Since they are of the same size, no scaling is needed, but the PIM software, if necessary, causes a slight rotation of one of the two images to be compared, so that they will both show the same view. It will be understood that in fact it is essential to "rotate" the electronic representations of the pixels in the image file Fj being considered, since the circuits that are responsible for the comparison are electronic circuits, so that the practitioner, and therefore display unit 80, do not take part during this step. Then, a shift of one of the two electronic images Fj, in abscissa and in ordinate, allows the PIM software to detect a correlation peak between the two images Fj, which are then positioned as well as possible. The difference between the two images Fj, the new one and the old one, therefore represents the evolution of the status of the tooth. Such an image "difference" may then be displayed, in shades of gray or color, with possibly bands of different colors depending on the difference being considered on each image point. The principle of such image presentation encodings was described above.

If an image is invalidated, the dental status slot being considered remains selected, and a new image taken overwrites the preceding image of the same tooth, On the other hand, validation of an image, as described above, is detected by the PIM2 software, which then goes to the next tooth, of rank sequence j+1 in the sequence, the next corresponding slot of the status then being selected to receive a next image, from an image file Fj+1.

Alternatively, if the order in the sequence of images to be taken is not the natural order of the row of teeth of the maxillary, the PIM2 software displays, i.e. points on the screen of display unit 80, the position of the tooth of which an image is to be taken in the natural order of the teeth.

In a polling step 316, the PIM2 software examines base 2 to see if it has received an image from image sensor 1, and, if not, branch NO, it performs a rewraparound of cyclic polling through a step 318 of time out (schematized by symbol θ) of predetermined duration. In the affirmative, branch YES, a step 320 takes place, in which the PIM software incorporates the current image file Fj in the client file Dp, i.e. the PIM2 software transmits, to PIM9 software, the image file Fj, which has been validated so that it is incorporated into the client file Dp.

In a next step 322, the PIM software goes to the next tooth, or digital place j+1 in the sequence, so that the dental status slot reserved for this tooth receives the image taken which corresponds to the image file Fj+1.

As discussed above, the PIM software may be stored exclusively in one of the elements that constitute PC 9 and the base 2, the other element being intended to remotely read the desired instructions therein. The PIM software is however conveniently spread into two parts PIM9 and PIM2 which communicate so that they act jointly. Base 2 and PC 9 may also access, through the above-mentioned data transmission network, a server which stores all, or part, of the PIM software, i.e. which offers, in real time, the functions of PIM software. The PIM software may also be stored on a data storage support, for example a floppy disk, an integrated circuit or also a mini hard disk. In particular, it is thus possible to use a standard PC 9, which has access to the PIM dental application software, implemented in this way or accessible through the network, and base 2 then contains only one restricted application nucleus, in order to access the PIM software using PC 9.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A system for taking dental images comprising:
    an image sensor for taking a dental image of a tooth of a patient, said image sensor being responsive to an intensity of radiation emitted by an external source of X-rays and being adapted to provide an electronic image corresponding to the tooth through which the radiation travels;
    a portable base for controlling said image sensor and for receiving said dental image from said image sensor, said portable base comprising:
        means for displaying a dental image;

sequencing means responsive to an action of a validation means used for validating at least one image file of dental images, at least one file being an image file of a said dental image, wherein the sequencing means are adapted to manage a library, for storing a sequence of files of said dental image files, and which are adapted to associate rank sequence data with each validated image file.

2. A system for taking dental images according to claim 1, wherein the sequencing means comprises a counter adapted so that it is incremented by the validation means to provide counting data at an output for validated image files belonging to said rank sequence data.

3. A system for taking dental images according to claim 2, wherein the sequencing means are adapted to write, in the library, the counting data in association with the image file being considered.

4. A system for taking dental images according to claim 2, wherein the sequencing means are adapted so that the counting data control a switching circuit which determines, from among a plurality of specified addresses, an address where to write, in the library, the image file being considered.

5. A system for taking dental images according to claim 2, wherein the sequencing means are adapted to write, in the library, the image files of all the images that were taken, whether validated or not, as well as the rank sequence data that is associated with validation data.

6. A system for taking dental images according to claim 2, wherein the sequencing means are adapted to write, in the library, the image files of all the images that were taken, whether validated or not, as well as all the rank sequence data that is associated with validation data, and the sequencing means are adapted to provide the said validation data in the form of time-dated data of the associated image file.

7. A system for taking dental images according to claim 1, wherein the library comprises a plurality of memory areas for a same plurality of patient files including some said files of dental images and which includes a care history of the patient considered, and wherein the base comprises a sleep/wake device that is arranged to control managing circuits of the library, provided for, according to information on a planned sequence of patients to be treated for one day, automatically selecting one of the memory areas of patient files and providing file information on the display means.

8. A system for taking dental images according to claim 1, wherein the base further comprises invalidation means for controlling invalidation of an image file.

9. A system for taking dental images according to claim 8, wherein the display means are adapted so that they automatically display a last image received by the base, and accessing means are provided for processing the image.

10. A system for taking dental images according to claim 8, wherein the display means are adapted for automatically displaying a last image received by the base, and processing means are provided for processing the image, including code conversion circuits adapted for converting gray levels, encoded on a scale of predetermined gray levels, into elements each having a specified color which belongs to a predetermined corresponding scale of colors.

11. A system for taking dental images according to claim 1, wherein the display means are adapted for automatically displaying a last image received by the base, and means are provided for processing the image, which include code conversion circuits arranged for converting gray levels, encoded on a predetermined scale of gray levels, into elements each having a specified color belonging to a predetermined corresponding scale of colors, and the base includes a man-machine interface unit that is adapted for controlling the displacement of a cursor in a predetermined range in order to cause a variation of connection between each level of the scale of gray and the associated specified color, wherein the cursor includes a wobulation circuit comprising a clock signal counter associated with control circuits which cyclically count between two limit values, in order to thus provide an upgradeable value of a conversion pitch between the scale of gray levels and the scale of colors.

12. A system for taking a dental image according to claim 1, wherein the base includes digital link means adapted for receiving, from an item outside the base, animated images that are provided at a given rate, and the display means are adapted for displaying said images.

13. A system for taking dental images according to claim 1, wherein the base further comprises digital link means adapted for receiving programming data from outside the base.

14. A system for taking dental images according to claim 1, wherein the base further comprises a housing, for receiving the image sensor at rest, associated with a detector of the presence of the image sensor adapted for controlling a standby/reviving device arranged for controlling managing circuits for managing the image sensor.

15. A system for taking dental images according to claim 1, wherein the base further comprises means for mounting the base on a piece of furniture.

16. A system for taking dental images according to claim 1, wherein the base further comprises a casing comprising a furniture element and a housing for receiving other parts of the base, with a window for displaying a screen of image display means and means for presenting a control element belonging to the image invalidating control means.

17. A system for taking dental images according to claim 1, wherein the base further comprises a casing comprising a furniture element and a housing for receiving other parts of the base, with a display window for the screen in the image display means and which has a control element belonging to the image invalidating control means, the housing of the casing extending, along a direction in which a support arm extends, and which constitutes the piece of furniture, partially in front of the window and partially in a section of the arm that has no window, and means for processing the image are grouped into a module which is separate from said screen and is connected to the screen with flexible wires.

18. A system for taking dental images according to claim 1, wherein the base further comprises a casing that comprising a piece of furniture and a housing for receiving other parts of the base, with a window that reveals a screen in image display means and which displays a control element belonging to image invalidating control means, with the base being adapted to be incorporated into either a support arm of a source of X-rays or a support bracket for dental tool.

19. A computer readable medium comprising computer programs including instructions to cause a computer operating system to manage the taking of dental images, characterized by the fact that it includes a series of instructions arranged so that, once they are made accessible to a computer operating system manage the reception of a sequence of dental image files.

20. A computer readable medium comprising computer programs according to claim 19, wherein the series of instructions are adapted so that the received images files are automatically filed in a predetermined order.

21. A computer readable medium comprising computer programs further including support for storing data, containing a software for managing the taking of images according to claim 19.

* * * * *